(12) United States Patent
Ueno

(10) Patent No.: US 6,414,021 B1
(45) Date of Patent: Jul. 2, 2002

(54) CONTROL OF INTRAOCULAR PRESSURE DURING SURGERY

(75) Inventor: Ryuji Ueno, Potomac, MD (US)

(73) Assignee: Sucampo AG, Zurich (CH)

( * ) Notice: Subject to any disclaimer, the term of this patent is extended or adjusted under 35 U.S.C. 154(b) by 0 days.

(21) Appl. No.: 09/645,361

(22) Filed: Aug. 25, 2000

(51) Int. Cl.$^7$ .................. A61K 31/215; A61K 31/19
(52) U.S. Cl. ................... 514/530; 514/573; 514/913
(58) Field of Search ................ 514/530, 573, 514/913

(56) References Cited

U.S. PATENT DOCUMENTS 5,001,153 A  *  3/1991  Ueno et al. .......... 514/530
5,212,196 A      5/1993  House et al.

* cited by examiner

*Primary Examiner*—Zohreh Fay
(74) *Attorney, Agent, or Firm*—Sughrue Mion, PLLC

(57) ABSTRACT

An ocular infusion solution containing a prostaglandin-like compound or prostaglandin-analog is used during ocular surgery for maintaining desired intraocular pressure of the patient.

13 Claims, 2 Drawing Sheets

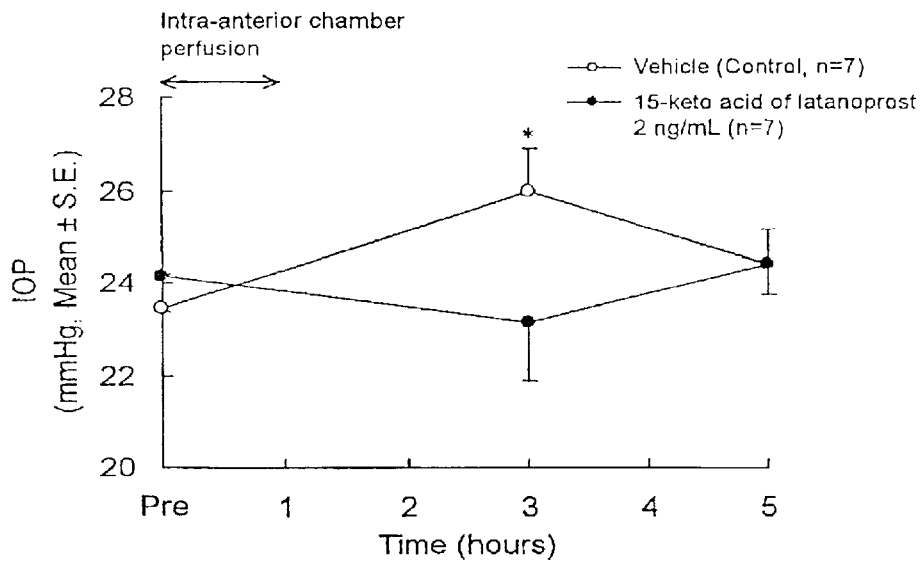

Fig. 1  Effect of intra-anterior chamber perfusion with 15-keto acid of latanoprost on intraocular pressure (IOP) in monkeys
The anterior chamber was perfused with 15-keto acid of latanoprost or the vehicle for 1 hour. The same eye was used for both treatments in a crossover way with a recovery period for at least 12 days.  *p < 0.05 compared with pre-treatment (paired t-test).

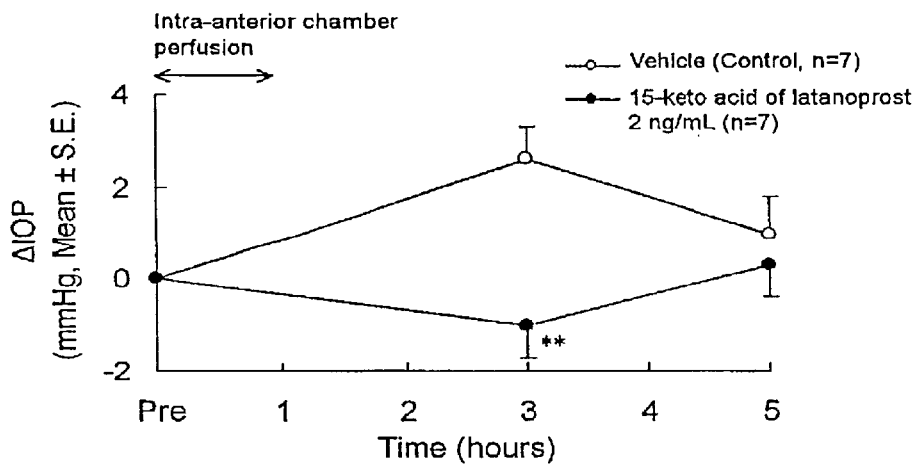

Fig. 2  Effect of intra-anterior chamber perfusion with 15-keto acid of latanoprost on intraocular pressure (IOP) in monkeys: Changes of IOP from pre-treatment value (ΔIOP)
The anterior chamber was perfused with 15-keto acid of latanoprost or the vehicle for 1 hour.  The same eye was used for both treatments in a crossover way with a recovery period for at least 12 days.  **p < 0.01 compared with vehicle treatment (Student's t-test).

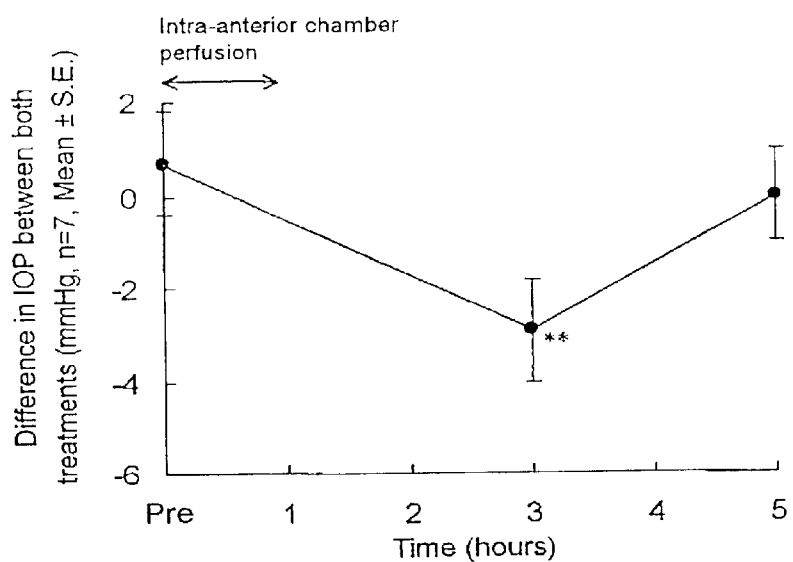

Fig. 3 Effect of intra-anterior chamber perfusion with 15-keto acid of latanoprost on intraocular pressure (IOP) in monkeys The anterior chamber was perfused with 15-keto acid of latanoprost (2 ng/mL) or the vehicle for 1 hour. The same eye was used for both treatments in a crossover way with a recovery period for at least 12 days. Difference in IOP: IOP in 15-keto acid of latanoprost treatment minus IOP in vehicle treatment  **p < 0.01 compared with pre-treatment (paired t-test).

CONTROL OF INTRAOCULAR PRESSURE DURING SURGERY

BACKGROUND OF THE INVENTION

The present invention relates to the regulation of intraocular pressure (IOP) during and immediately after eye surgery. IOP can increase during and following both invasive eye surgery, for example, cataract surgery, glaucoma surgery and vitrectomy, and non-invasive eye surgery, for example, non-invasive laser surgery.

In the prior art, systemic IOP lowering agents such as carbonic anhydrase inhibitors, acetazolamide, and the like, as well as systemically administered hyperosmotic agents such as mannitol, glycerin, and the like, have been used for treating the IOP increase occurring during and after surgery. More recently, so called clonidines or substituted phenyliminoimidazolines have been employed as topical eye drops applied preoperatively in order to provide decreased IOP over a relatively short period, i.e., 1–24 hours prior to the surgical procedure, followed by subsequent application after surgery for controlling post-operative IOP. See U.S. Pat. No. 5,212,196.

SUMMARY OF THE INVENTION

The present invention provides another solution to the problem of maintaining normal or below normal IOP during and immediately after eye surgery without the need for topical application of an IOP reducing agent in the form of drops or ointment prior to eye surgery and/or immediately after eye surgery.

In one embodiment of the present invention, a prostaglandin-like IOP reducing agent of the type providing extremely low side effects is infused into the eye during surgery as part of a conventional ophthalmic surgical infusion or rinsing solution.

In a preferred embodiment of the present invention, the active agent is a 13,14-dihydro-15-keto prostaglandin having an extended straight chain omega chain, or having a shortened omega chain containing a ring.

In preferred embodiments at present, isopropyl unoprostone, which is 13,14-dihydro-15-keto-20-ethyl PGF$_2\alpha$ isopropyl ester (a docosanoid), 15-keto-latanoprost, which is 13,14-dihydro-15-keto-18,19,20-trinor-17-phenyl PGF$_2\alpha$ isopropyl ester, or 13,14-dihydro-15-keto-travoprost, which is 13,14-dihydro-15-keto-17,18,19,20-tetranor-16-(m-trifluoromethylphenoxy)-PGF$_2\alpha$ isopropyl ester, is used as an active drug. In a particularly preferred embodiment at present, the active agent is isopropyl unoprostone and/or 15-keto-latanoprost. In another preferred embodiment, the ophthalmic infusion is an artificial aqueous humor. In still another preferred embodiment, the active drug is a PGF type compound.

DESCRIPTION OF THE DRAWING

FIGS. 1, 2, and 3 depict the results of Example 2.

DETAILED DESCRIPTION OF THE INVENTION

The present invention provides ocular infusing or rinsing solutions useable during ocular surgery for regulating IOP during and immediately (for several hours up to about 1 day) following surgery.

The infusion or rinsing solution is a known ophthalmic infusing or rinsing solution, examples for which are provided below.

The active IOP reducing agent is selected from prostaglandin-like or prostaglandin analog compounds that provide little if any hyperemia or ocular irritation. Two preferred compounds of this type are the above-noted 15-keto latanoprost and the above-noted unoprostone.

The compounds usable in the present invention can be of the PGA, PGB, PGC, PGD, PGE, PGF, or PGJ type and include subtypes 1, 2, and 3.

The intraocular pressure reducing agents which should be useable in the present invention have the formula I:

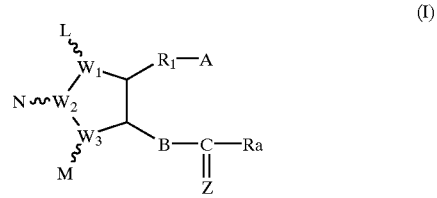

(I)

wherein $W_1$, $W_2$ and $W_3$ are carbon or oxygen atoms,
L, M and N are hydrogen, hydroxy, halogen, lower alkyl, hydroxy(lower)alkyl, or oxo, wherein at least one of L and M is a group other than hydrogen, and the five-membered ring may have one or more double bond(s);
A is —CH$_2$OH, —COCH$_2$OH, —COOH or its functional derivative;
B is —CH$_2$—CH$_2$—, —CH=CH— or —C≡C—;
Z is

wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;
$R_1$ is a divalent saturated or unsaturated lower-medium aliphatic hydrocarbon residue, which is unsubstituted or substituted by halogen, oxo, hydroxy, lower alkyl, aryl or heterocyclic group; and
Ra is a saturated or unsaturated lower-medium aliphatic hydrocarbon residue, which is unsubstituted or substituted by halogen, oxo, lower alkyl, hydroxy, lower alkoxy, lower alkanoyloxy, cyclo(lower)alkyl, cyclo(lower)alkyloxy, aryl, aryloxy, heterocyclic group or heterocyclic-oxy group; or a cyclo(lower)alkyl; cyclo(lower)alkyloxy; an aryl; an aryloxy; a heterocyclic group; or a heterocyclic-oxy group.

A group of more preferred compounds used in the present invention has the formula (II):

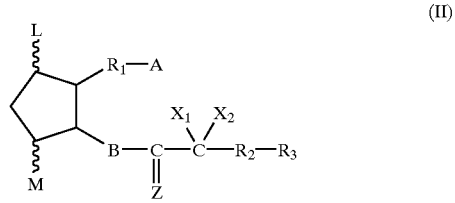

(II)

wherein L and M are hydrogen, hydroxy, halogen, lower alkyl, hydroxy(lower)alkyl, or oxo, wherein at least one of L and M is a group other than hydrogen, and the five-membered ring may have one or more double bond(s);

A is —CH$_2$OH, —COCH$_2$OH, —COOH or its functional derivative;

B is —CH$_2$—CH$_2$—, —CH=CH— or —C≡C—;

Z is

wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

X$_1$ and X$_2$ are hydrogen, lower alkyl, or halogen;

R$_1$ is a divalent saturated or unsaturated lower-medium aliphatic hydrocarbon residue, which is unsubstituted or substituted by halogen, oxo, hydroxy, lower alkyl, aryl or heterocyclic group;

R$_2$ is a single bond or lower alkylene; and

R$_3$ is lower alkyl, lower alkoxy, cyclo(lower)alkyl, cyclo(lower)alkyloxy, aryl, aryloxy, heterocyclic group or heterocyclic-oxy group.

In the above formula, the term "unsaturated" in the definitions for R$_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions. Preferred unsaturated bonds are a double bond at position 2 and a double or triple bond at position 5.

The term "lower-medium aliphatic hydrocarbon" means a hydrocarbon having a straight or branched chain of 1 to 14 carbon atoms, wherein the side chain has preferably 1 to 3 carbon atoms. The preferred R$_1$ has 1 to 10, more preferably, 1 to 8 carbon atoms, and the preferred Ra has 1 to 10, more preferably, 1 to 8 carbon atoms.

The term "halogen" includes fluorine, chlorine, bromine, and iodine.

The term "lower" means a group having 1 to 6 carbon atoms unless otherwise specified.

The term "lower alkyl" means a straight- or branched-chain saturated hydrocarbon group having 1 to 6 carbon atoms, for example, methyl, ethyl, propyl, isopropyl, butyl, isobutyl, t-butyl, pentyl, and hexyl.

The term "lower alkoxy" means a lower alkyl-O— wherein the lower alkyl is as described above.

The term "hydroxy(lower)alkyl" means an alkyl as described above, which is substituted by at least one hydroxy group, for example, hydroxymethyl, 1-hydroxyethyl, 2-hydroxyethyl, and 1-methyl-1-hydroxyethyl.

The term "lower alkanoyloxy" means a group represented by the formula RCO—O—, wherein RCO— is an acyl formed by oxidation of a lower alkyl as described above, for example, acetyl.

The term "lower cycloalkyl" means a group formed by cyclization of a lower alkyl group containing 3 or more carbon atoms as described above, for example, cyclopropyl, cyclobutyl, cyclopentyl, and cyclohexyl.

The term "cyclo(lower)alkyloxy" means a group represented by the formula cycloalkyl-O—, wherein cycloalkyl is described above.

The term "aryl" includes aromatic hydrocarbon rings (preferably monocyclic groups) which may be substituted, for example, phenyl, tolyl and xylyl. Examples of the substituent in this case include halogen, and halogen substituted lower alkyl group, wherein halogen atom and lower alkyl group are as described above.

The term "aryloxy" means a group represented by the formula ArO—, wherein Ar is an aryl group as described above.

The term "heterocyclic group" includes mono- to tricyclic, preferably monocyclic heterocyclic group which is 5 to 14, preferably 5 to 10 membered ring having optionally substituted carbon atom and 1 to 4, preferably 1 to 3 of 1 or 2 types of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazyl, pyrimidyl, pyrazyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, puryl, quinazolinyl, carbazolyl, acridinyl, phenanthridinyl, benzimidazolyl, benzimidazolonyl, benzothiazolyl, and phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters, and amides.

Examples of suitable "pharmaceutically acceptable salts" include nontoxic salts which are commonly used, and salts with inorganic bases, for example, alkali metal salts (sodium salt, potassium salt and the like); alkaline earth metal salts (calcium salt, magnesium salt and the like); ammonium salts; salts with organic bases, for example, amine salts (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, lysine salt, procaine salt, and caffeine salt); basic amino acid salts (such as arginine salt, and lysine salt); tetraalkyl ammonium salts and the like. These salts may be manufactured from, for example, corresponding acids and bases in accordance with a conventional manner or salt exchange.

Examples of the ethers include aliphatic ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester, and 1-cyclopropylethyl ester; lower alkenyl esters such as vinyl ester, and allyl ester; lower alkynyl esters such as ethynyl ester, and propynyl ester; hydroxy(lower)alkyl esters such as hydroxyethyl ester; and lower alkoxy(lower)alkyl esters such as methoxymethyl ester, and 1-methoxyethyl ester as well as, for example, optionally substituted aryl esters such as phenyl ester, tosyl ester, t-butylphenyl ester, salicyl ester, 3,4-dimethoxyphenyl ester, and benzamidephenyl ester; and aryl(lower)alkyl esters such as benzyl ester, trityl ester, and benzhydryl ester. An example of amides includes mono- or di-lower alkyl amides such as methylamide, ethylamide, and dimethylamide; aryl amides such as anilide, and toluidide; and alkyl or aryl sulfonyl amides such as methylsulfonyl amide, ethylsulfonyl amide, and tolylsulfonyl amide.

Preferred examples of L and M include hydroxy and oxo.

Preferred examples of A-group include —COOH, and a pharmaceutically acceptable salt, an ester and an amide thereof.

A preferred example of B is —$CH_2$—$CH_2$— which provides the structure of so-called, 13,14-dihydro type.

Preferred examples of Z is =O which provides the structure of so-called, 15-keto-type.

The configuration of the ring and the α- and/or omega chain in the above formulas (I) and (II) may be the same as or different from that in the primary PGs. However, the present invention also includes a mixture of a compound having a primary configuration and that of an unprimary configuration.

The compounds having 15-keto group may be in the keto-hemiacetal equilibrium by forming a hemiacetal between hydroxy group at position 11 and ketone at position 15.

The proportion of both tautomeric isomers, when present, varies depending on the structure of the rest of the molecule or kind of any substituent present and, sometimes, one isomer may predominately be present in comparison with the other. However, in this invention, it is to be appreciated that the compounds used in the invention include both isomers. Further, while the compounds used in the invention may be represented by a structure or name based on keto-form regardless of the presence or absence of the isomers, it is to be noted that such structure or name does not intend elimination of the hemiacetal type of compounds.

In the present invention any of the individual tautomeric isomers, a mixture thereof, or optical isomers, a mixture thereof, a racemic mixture, and other isomers such as steric isomers can be used in the same purpose.

Other species compounds useable in the present invention are disclosed in U.S. Pat. Nos. 5,001,153, 5,166,178 and 5,321,128.

The active agent can be instilled into the eye during ophtahnic surgery as part of an otherwise conventional ophthalmic surgical infusion or rinsing solution. Any of the known ocular infusion or rinsing solutions used during ocular surgery, as long as an incompatibility does not exist between it and the active agent (which can easily be determined) are useable in the practice of the present invention. Non-limiting examples are:

(1) Artificial aqueous humor, such as Opeguard-MA available from Senjyu Pharmaceutical Co., Ltd., which contains Glucose 0.15%, NaCl 0.66%, KCl 0.036%, $CaCl_2$ 0.018%, $MgSO_4$ 0.03%, $NaHCO_3$ 0.21%, pH 6.7 to 8.2, osmotic pressure ratio: 0.86 to 1.14.

(2) Ringer's solution (USP, JP): NaCl 0.86%, KCl 0.03%, $CaCl_2$ 0.033%, pH 5.0 to 7.5, osmotic pressure ratio: about 1.

(3) Lactated Ringer's solution (USP, JP): NaCl 0.6%, sodium lactate 0.31%, KCl 0.03%, $CaCl_2$ 0.02%, pH 6.0 to 7.5, osmotic pressure ratio: 0.8 to 1.0.

(4) BSS (Balanced Salt Solution), Alcon: NaCl 0.64%, KCl 0.075% $CaCl_2$ 0.048%, $MgCl_2$ 0.03%, sodium acetate 0.39%, sodium citrate 0.17%, HCl/NaOH (5) BSS Plus (Balanced Salt Solution Enriched with Bicarbonate, Dextrose and Glutathione): NaCl 0.714%, KCl 0.038%, $CaCl_2$ 0.0154%, $MgCl_2/6H2O$ 0.02%, $Na_2HPO_4$ 0.042%, $NaHCO_3$ 0.21%, Dextrose 0.092%, Gluthathione disulfide 0.0184%, HCl/NaOH, pH about 7.4, osmorality 305 mOs (osmotic pressure ratio: 1.07).

The concentration of the active agent in the infusion or rinsing solution can easily be determined by routine experimentation. A range of about 10 pg/ml to 100 mg/ml will often be acceptable, preferably about 100 pg/ml to 10 mg/ml

EXAMPLE 1

The intraocular pressure lowering effect of 15-keto acid of latanoprost (13,14-dihydro-15-keto-17-phenyl-18,19,20-trinor-$PGF_{2\alpha}$) by perfusion in the anterior chamber in monkeys was investigated. It was demonstrated that intraocular pressure was lowered by perfusion in the anterior chamber with 15-keto acid of latanoprost Materials and Methods 1. Test Substance 15-keto acid of latanoprost 2. Animals Male cynomolgus monkeys (body weight: 4.5–6.5 kg) were used. These monkeys were housed individually in cages for monkeys in a room which was maintained at room temperature of 24±1° C., relative humidity of 55±10%, ventilation of about 12 times/hour and a 12-hour light-dark cycle (fluorescent lighting: 8:00 a.m. to 8:00 p.m). The animals were given solid food for monkeys (PS, Oriental Yeast Co., Ltd.), vegetables and fruits, and allowed free access to tap water from an automatic dispenser. The healthy animals without abnormalities in the anterior segment of the eye were used in this study.

3. Preparation of Dosing Solution

In the present study the solution containing 59 ng/mL of 15-keto acid of latanoprost was adjusted with commercially available intraocular perfusate (Opeguard-MA, Lot P-464, Senju Pharmaceutical Co., Ltd.). The control solution (vehicle) was the intraocular perfusate.

4. Administration Method of Test Substance

The animals were anesthetized by the injection intramuscularly with 5.0–7.5 mg/kg of ketamine hydrochloride (Ketalar®50, Sankyo Co., Ltd.), and restrained in a supine position. In operation and perfusion of the dosing solution in the anterior chamber, the anesthesia was maintained by intramuscular injection of 5 mg/kg of ketamine at interval of 30 minutes. Two 30 G injection needles (one for infusion of the dosing solution and the other for discharge, Becton Dickinson) were inserted into the anterior chamber from the temporal corneal ring of the eye ball. After aqueous humor in the anterior chamber was aspirated through a needle for the discharge, 15-keto acid of latanoprost solution or vehicle was infused at the rate of 50 µL/min through a needle for infusion for 1 hour, using a syringe pump (KBS model 100, Neuro Science). The flow resistance of the perfusate was adjusted by the length of the cannula (PE10) connected to the needle for discharge and the anterior internal pressure was maintained at about 20 mmHg level. The test solution or vehicle was perfused in the same eye at the intervals of 3 weeks.

5. Measurement of IOP

After the ocular surface of monkeys was anesthetized by instillation of 0.4% oxybuprocaine hydrochloride (Benoxil® 0.4% solution, Santen Pharmaceutical Co., Ltd.) under i.m. systemic anesthesia with 5 mg/kg of ketamine hydrochloride, IOP was measured with an applanation pneumatonograph (Alcon Japan Ltd.). IOP was measured before perfusion of the test substance and 2 and 4 hours after perfusion (3 and 5 hours, respectively, after the start of the perfusion of the test substance). The mean value of the IOP measured twice at 30-minute interval before perfusion was used as IOP before perfusion of the test substance. The difference between the change values of IOP (from IOP before perfusion) after perfusion of 15-keto acid of latanoprost solution and change values of IOP (from IOP before perfusion) after perfusion of the vehicle was regarded as change values of IOP due to 15-keto acid of latanoprost.

6. Experimental Group

| Group | Concentration | Perfusion | | n |
|---|---|---|---|---|
| | | Rate | Time | |
| Vehicle (control) | — | 50 µL/min | 1 hr | 2 |
| 15-keto acid of latanoprost | 59 ng/mL | 50 µL/min | 1 hr | 2 |

Results

In the present study, 15-keto acid of latanoprost solution (59 ng/mL of the solution) or vehicle was perfused in the anterior chamber of monkey eyes for 1 hour and IOP was measured before perfusion and with time after perfusion to investigate the effect of 15-keto acid of latanoprost on IOP.

When 15-keto acid of latanoprost solution was perfused in the anterior chamber of monkeys for 1 hour, 2.8 and 2.3 mmHg of IOP decreased at 3 and 5 hours, respectively, after the start of perfusion (2 and 4 hours after the end of perfusion of the dosing solution for 1 hour), as compared with changes in IOP of the control animal after perfusion of the vehicle for 1 hour.

EXAMPLE 2

The effects on intraocular pressure by intra-anterior chamber perfusion with a lower dosage of 13,14-dihydro-15-keto-17-phenyl-18,19,20-trinor-PGF$_2$ $_\alpha$ (15-keto acid of latanoprost) were investigated in monkeys. One hour perfusion in the anterior chamber with 15-keto acid of latanoprost at the concentration (2 ng/mL) was carried out.

MATERIALS AND METHODS

1. Test Substance 13,14-dihydro-15-keto-17-phenyl-18,19,20-trinor-PGF$_2$ α (15-keto acid of latanoprost)

2. Preparation of Dosing Solution

The solution containing 15-keto acid of latanoprost at 2 ng/mL was prepared with a commercially available intraocular perfusate (Opeguard MA, Senju Pharmaceutical Co. Ltd.) as a vehicle.

3. Animals

Seven male cynomolgus monkeys (Body weight: 3.9–6.0 kg) purchased from Kasyo Co., Ltd. were used. These monkeys were housed individually in cages in a room which was maintained at room temperature of 24±1° C., relative humidity of 55±10%, ventilation rate of about 12 times/hour and 12-hour light-dark cycle (fluorescent lighting: 8:00 to 20:00). The animals were given food pellets for monkeys (PS, Oriental Yeast Co., Ltd.), vegetables and fruits once a day, and allowed free access to tap water from an automatic dispenser. The healthy animals without abnormalities in the anterior segment of the eye were used in this study.

4. Intra-anterior Chamber Perfusion

The animals were anesthetized by an intramuscular injection of 5.0–7.5 mg/kg of katamine hydrochloride (Ketalar 50, Sankyo Co., Ltd.), and restrained in a supine position. Two 30 G injection needles (one for infusion of the dosing solution and the other for discharge, Becton Dickinson and Co.) connected to polyethylene cannula (PE10, Becton Dickinson and Co.) were inserted into the anterior chamber from the temporal corneal ring of the eye ball. The anterior chamber was perfused with the 15-keto acid of latanoprost solution or the vehicle at a rate of 40 µL/min through the cannula for 1 hour using a syringe pump (Model 100, KD Scientific Inc.). During the perfusion, the anesthesia was maintained by intramuscular injection of 5.0 mg/kg ketamine hydrochloride every 20 minutes.

5. Measurement of Intraocular Pressure

The animals were systemically anesthetized by an intramuscular injection of 5.0–7.5 mg/kg of ketamine hydrochloride (Ketalar 50, Sankyo Co., Ltd.), and the ocular surface was anesthetized by a instillation of 0.4% oxybuprocaine hydrochloride (Benoxil 0.4% solution, Santen Pharmaceutical Co., Ltd.). The animals were fixed in a supine position, and the intraocular pressure was measured by use of a pneumatonometer (Model 30 Classic, Mentor O & O.) before, and 3 and 5 hours after starting the perfusion (2 and 4 hours after stopping the perfusion, respectively).

6. Test Groups

| Group | Concentration | Perfusion | | N |
|---|---|---|---|---|
| | | Rate | Time | |
| Vehicle (Control) | — | 40 µL/min | 1 hour | 7 |
| 15-keto acid of latanoprost | 2 ng/mL | 40 µL/min | 1 hour | 7 |

The animals were used two times. The same eye of each animal was used for both treatments in a crossover way with a recovery period for at least 12 days.

7. Statistical Analysis

The data were statistically analyzed with Student's t-test or paired t-test. P values less than 0.05 were considered to be statistically significant.

RESULTS

The intra-anterior chamber perfusion with the vehicle for 1 hour resulted in a significant increase in the intraocular pressure of 2.6 mmHg 3 hours after starting the perfusion as compared with the pre-treatment value (FIG. 1, FIG. 2, Table 1). On the other hand, the intra-anterior chamber perfusion with the 2 ng/mL soluton of 15-keto acid of latanoprost lowered the intraocular pressure by 1.0 mmHg 3 hours after starting the perfusion as compared with the pre-treatment value. The reduction in the intraocular pressure with 15-keto acid of latanoprost was significant as compared with vehicle treatment (FIG. 2 , Table 1). The difference in the intraocular pressure between both treatments at matched time was compared between before and after the perfusion. A significant reduction in the intraocular pressure by the perfusion with 15-keto acid of latanoprost was shown 3 hours after starting the perfusion as well (FIG. 3, Table 1).

In the present study, the effect on intraocular pressure by intra-anterior chamber perfusion with 15-keto acid of latanoprost at the concentration (2 ng/mL) was investigated in monkeys. The intra-anterior chamber perfusion with the 2 ng/mL solution of 15-keto acid of latanoprost resulted in a significant reduction in the intraocular pressure.

TABLE 1

| Time after starting perfusion | 15-keto acid of latanoprost (2 ng/mL) | | Vehicle (Control) | | Difference in IOP between both treatments[2] (mmHg) |
| --- | --- | --- | --- | --- | --- |
| | IOP (mmHg) | ΔIOP[1] (mmHg) | IOP (mmHg) | ΔIOP[1] (mmHg) | |
| Before perfusion | 24.1 ± 0.8 | — | 23.4 ± 0.8 | — | 0.7 ± 1.1 |
| 3 hours | 23.1 ± 1.3 | −1.0 ± 0.7** | 26.0 ± 0.9§ | 2.6 ± 0.7 | −2.9 ± 1.1## |
| 5 hours | 24.4 ± 0.7 | 0.3 ± 0.7 | 24.4 ± 0.7 | 1.0 ± 0.8 | 0.0 ± 1.0 |

The anterior chamber was perfused with 15-keto acid of latanoprost or the vehicle for 1 hour. The same eye was used for both treatments in a crossover way with a recovery period for at least 12 days. The values are mean ± S.E. of 7 animals.
[1]ΔIOP: Changes of IOP from pre-treatment value.
[2]Difference in IOP: IOP in 15-keto acid of latanoprost treatment minus IOP in vehicle treatment.
**$p < 0.01$ compared with vehicle treatment (Student's t-test).
§$p < 0.05$ compared with pretreatment (paired t-test).
$p < 0.01$ compared with pre-treatment (paired t-test).

Variations of the invention will be apparent to the skilled artisan.

We claim:

1. A process for maintaining an acceptable intraocular pressure during ocular surgery in an eye of a patient which comprises infusing into the eye an ophthalmic surgical infusion or rinsing solution containing an effective amount for maintaining acceptable intraocular pressure of a compound of the formula (I):

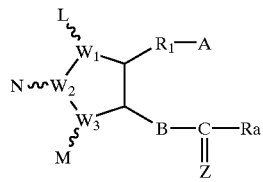

wherein $W_1$, $W_2$ and $W_3$ are carbon or oxygen atoms,

L, M and N are hydrogen, hydroxy, halogen, lower alkyl, hydroxy(lower)alkyl, or oxo, wherein at least one of L and M is a group other than hydrogen, and the five-membered ring may have one or more double bond(s);

A is —CH$_2$OH, —COCH$_2$OH, —COOH or its functional derivative;

B is —CH$_2$—CH$_2$—, —CH═CH— or —C≡C—;

Z is

wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$R_1$ is a divalent saturated or unsaturated lower-medium aliphatic hydrocarbon residue, which is unsubstituted or substituted by halogen, oxo, hydroxy, lower alkyl, aryl or heterocyclic group; and Ra is a saturated or unsaturated lower-medium aliphatic hydrocarbon residue, which is unsubstituted or substituted by halogen, oxo, lower alkyl, hydroxy, lower alkoxy, lower alkanoyloxy, cyclo(lower)alkyl, cyclo(lower)alkyloxy, aryl, aryloxy, heterocyclic group or hetrocyclic-oxy group; or a cyclo(lower)alkyl; cyclo(lower)alkyloxy; an aryl; an aryloxy; a heterocyclic group; or a heterocyclic-oxy group.

2. The process of claim 1 in which the effective amount of the compound of formula I prevents intraocular pressure from increasing during ocular surgery.

3. The process of claim 1 wherein the effective amount of the compound of formula I lowers intraocular pressure during ocular surgery to a value below that existing prior to surgery.

4. The process of claim 1 in which the infusing solution is infused into the eye during the surgery.

5. The process of claim 1 in which the infusing solution containing the compound of formula I is infused into the eye prior to the surgery.

6. The process of claim 1 wherein the infusion solution containing the compound of formula I is infused into the eye prior to and during surgery.

7. The process of claim 1 in which the infusing solution containing the compound of formula I is infused into the eye after the surgery.

8. The process of claim 1 wherein the infusion solution containing the compound of formula I is infused into the eye prior to, during and after ocular surgery.

9. The process of claim 1 in which the compound of formula (I) is isopropyl unoprostone.

10. The process of claim 1 in which the compound of formula (I) is 15-keto latanoprost.

11. The process of claim 1 wherein the surgery is non-invasive.

12. The process of claim 1 wherein the surgery is invasive.

13. The process of claim 11 wherein the surgery is laser surgery.

* * * * *